United States Patent
Marrone et al.

(10) Patent No.: US 12,030,837 B2
(45) Date of Patent: Jul. 9, 2024

(54) PROCESS FOR PRODUCING BIURET FROM UREA

(71) Applicant: Casale SA, Lugano (CH)

(72) Inventors: Leonardo Marrone, Mercallo (IT);
Alberto Benedetti, Como (IT);
Pierdomenico Biasi, Como (IT);
Cristina Pizzolitto, Como (IT)

(73) Assignee: Casale SA, Lugano (CH)

( * ) Notice: Subject to any disclaimer, the term of this patent is extended or adjusted under 35 U.S.C. 154(b) by 0 days.

(21) Appl. No.: 18/037,704

(22) PCT Filed: Aug. 31, 2021

(86) PCT No.: PCT/EP2021/073963
§ 371 (c)(1),
(2) Date: May 18, 2023

(87) PCT Pub. No.: WO2022/106083
PCT Pub. Date: May 27, 2022

(65) Prior Publication Data
US 2023/0322660 A1    Oct. 12, 2023

(30) Foreign Application Priority Data
Nov. 18, 2020    (EP) .................................. 20208473

(51) Int. Cl.
*C07C 275/62*    (2006.01)
(52) U.S. Cl.
CPC .................. *C07C 275/62* (2013.01)

(58) Field of Classification Search
CPC ................................................... C07C 275/62
See application file for complete search history.

(56) References Cited

U.S. PATENT DOCUMENTS 3,281,464 A * 10/1966 Tsao ...................... C07C 273/16
564/72
4,645,860 A * 2/1987 Green, II ............ C07C 273/189
564/73

(Continued)

FOREIGN PATENT DOCUMENTS

EP    1076934 A  * 9/1964  ............. C07D 55/36
GB    926781 A    5/1963

OTHER PUBLICATIONS

International Search Report issued Oct. 4, 2021 in connection with PCT Application No. PCT/EP2021/073963.

(Continued)

Primary Examiner — Michael L Leonard
(74) Attorney, Agent, or Firm — Akerman LLP

(57) ABSTRACT

A process for the production of biuret from urea wherein: a urea aqueous solution (24) withdrawn from the recovery section of a urea plant is processed to remove water and obtain a concentrated urea melt (25); said urea melt is processed under biuret-forming conditions to decompose urea into biuret and ammonia and obtain a high-biuret urea melt (26); said high-biuret urea melt (26) is diluted with water or with an aqueous stream obtaining a solution (28); the solution (28) is subject to crystallization and precipitation of a solid phase containing biuret which is separated from the aqueous phase.

25 Claims, 4 Drawing Sheets

(56) References Cited

U.S. PATENT DOCUMENTS

| | | | |
|---|---|---|---|
| 4,654,441 A * | 3/1987 | Stephan | ............ C07C 273/1881 |
| | | | 564/38 |
| 2008/0039623 A1 | 2/2008 | Lee et al. | |
| 2008/0286472 A1 * | 11/2008 | Tutin | ...................... C08L 61/00 |
| | | | 427/350 |

OTHER PUBLICATIONS

Written Opinion of the International Searching Authority issued Oct. 4, 2021 in connection with PCT Application No. PCT/EP2021/073963.

International Preliminary Report on Patentability issued Feb. 22, 2023 in connection with PCT Application No. PCT/EP2021/073963.

* cited by examiner

PROCESS FOR PRODUCING BIURET FROM UREA

CROSS-REFERENCE TO RELATED APPLICATIONS

This application is a national phase of PCT/EP2021/073963, filed Aug. 31, 2021, and claims priority to EP 20208473.7, filed Nov. 18, 2020, the entire contents of both of which are hereby incorporated by reference.

FIELD OF THE INVENTION

The present invention relates to a process for the production of biuret from urea. The invention further relates to integration of a process for obtaining a product which comprises predominantly biuret and urea with a conventional production of urea.

PRIOR ART

Urea is produced industrially by reacting ammonia and carbon dioxide at suitable urea-forming conditions, typically at a high pressure and high temperature.

Urea is synthesized at a synthesis pressure above 100 bar obtaining a reaction effluent containing urea, water and unconverted reagents mostly in the form of ammonium carbamate. Due to the equilibrium reached in the reaction environment, the amount of unconverted matter in the reaction effluent is significant and the reaction effluent is normally processed for its recovery.

To this purpose, the reaction effluent is normally processed in a recovery section at a pressure lower than the synthesis pressure, obtaining a recycle solution containing the reagents removed from the effluent, and a purified aqueous solution of urea. Said purified solution typically contains around 65-70% urea, the balance being water and unavoidable impurities. The process of recovery normally includes heating the solution to decompose ammonium carbamate and remove a gaseous phase containing ammonia and carbon dioxide, and condensing said gaseous phase to obtain a recycle solution.

In the widely used stripping processes, the effluent of a high-pressure reactor is heated in a high-pressure stripper, possibly in the presence of a stripping agent, to decompose the ammonium carbamate and extract gaseous ammonia and carbon dioxide. These are condensed in a high-pressure condenser and recycled to the synthesis reactor. When used, the stripping agent is generally gaseous carbon dioxide or gaseous ammonia.

Said high-pressure stripper and high-pressure condenser may operate at substantially the same pressure as the synthesis reactor, thus forming a high-pressure synthesis section or loop. The urea-containing effluent of the stripper is then processed in one or more recovery sections as described above.

Many applications require urea in a solid form. The production of solid urea is also termed finishing or product-shaping.

The most common techniques for urea shaping include prilling and granulation. In both cases, the purified urea solution from the recovery section is treated to remove water, e.g. in a suitable evaporation section to obtain a urea melt. Formaldehyde is also added to the urea melt before granulation or prilling, to improve the mechanical properties of the product, particularly the crushing strength.

It is known that urea is subject to thermal decomposition into biuret and ammonia. In the conventional production of urea, biuret is considered an undesired by-product and efforts are made to avoid its formation. Most applications of urea, such as fertilizer-grade urea or technical-grade urea, require a content of biuret not greater than 1.0% by weight.

The biuret, however, may be a valuable product for certain applications. For example biuret is a useful source of non-protein nitrogen (NPN) for cattle feed. The current production of biuret from urea involves basically dissolving the commercial solid urea to form a urea melt, and maintaining the so obtained melt in a batch reactor at a suitable temperature around 160° C., deep vacuum and for a suitable residence time for thermal decomposition of urea.

The above process is not suitable to provide a high capacity of production.

Another disadvantage of the above process is that commercial solid urea normally contains formaldehyde added during the shaping process. Formaldehyde poses serious health concerns and may not be desired or not accepted e.g. in a feed-grade biuret for cattle. Solid urea with no formaldehyde (e.g. technical-grade urea) is expensive and available in limited quantity, thus not adapted for a continuous process with a high capacity of production of biuret. Furthermore a batch process as in the prior art is generally not suitable to provide a high capacity of production.

A method and device for preparing biuret is disclosed in US 2008/039623.

SUMMARY OF THE INVENTION

The invention aims to solve the above drawbacks. The invention aims to a process adapted for production of biuret free of formaldehyde and adapted for a high capacity of production.

The above problem is solved with a process according to claim 1.

According to the invention, a urea aqueous solution, which is withdrawn from the recovery section of a urea production plant, is used for the production of high-biuret urea (HBU). The term high-biuret urea denotes a product which consists predominantly of biuret and urea. For example a HBU may contain at least 55% by weight of biuret and preferably at least 70% by weight. The sum of biuret and urea in the HBU at least 80% by weight.

The production of HBU from the urea aqueous solution includes:
- removing water, e.g. by evaporation, obtaining a urea melt preferably with concentration higher than 99.5% wt, more preferably higher than 99.7% wt;
- processing the urea melt under biuret-forming conditions to decompose urea into biuret and ammonia and obtain a biuret-containing urea melt;
- diluting the biuret-containing urea melt with water or with an aqueous stream obtaining a solution;
- crystallization of said solution, including precipitation of a solid phase containing biuret and obtaining a slurry including precipitated solid phase and a mother liquor;
- separation of a solid product containing biuret from the slurry;
- optionally, a further step of removing water from said solid product, e.g. with a drying process.

The biuret-containing solid product may be in the form of granules or powder.

The invention provides a process for the production of biuret which can be fully integrated with a conventional urea process. By withdrawing urea solution from a recovery section of a urea plant, the production of biuret can be coupled with the conventional production of low-biuret urea (LBU). The term low-biuret urea denotes urea for uses wherein biuret is an undesired by-product. The content of biuret in the LBU is typically not greater than 1.5% or 1.0% by weight.

The biuret can be produced in-line by continuously withdrawing urea solution from the recovery section of a urea plant. Therefore the process of the invention is suitable for a large capacity in terms of production, e.g. tons of biuret per day.

The integration with a urea production process is also advantageous for the recycle of the ammonia liberated in the decomposition of urea. The decomposition of urea into biuret produces also gaseous ammonia which, in the present invention, can be efficiently recycled to the tied-in urea production process.

Still another advantage of the invention is that the urea solution withdrawn from the recovery section can be sent to production of biuret before any addition of formaldehyde. Therefore a biuret free of formaldehyde can be obtained in parallel with the production of conventional LBU containing formaldehyde as a shaping additive.

In a preferred embodiment, a first portion of the urea solution obtained from the recovery section is processed to produce high-biuret urea and a second portion of said solution is processed separately to produce conventional low-biuret urea. The formaldehyde, if needed, can be added only to the second portion.

The invention further relates to a plant according to the claims. The plant is an integrated plant for the production of high-biuret urea and of low-biuret urea.

The invention can be applied to all processes for the production of urea including in particular the total-recycle process and the stripping processes. The invention can also be applied to an existing urea plant. An existing urea plant can be modified by adding a high-biuret urea production section and by sending at least part of the solution from the recovery section to the newly installed high-biuret urea production section. A urea plant can be adapted for production of HBU in parallel with the conventional production of LBU.

DESCRIPTION OF PREFERRED EMBODIMENTS

The urea aqueous solution used for the production of the HBU can be substantially free of formaldehyde. Particularly, this urea solution does not contain added formaldehyde. If any, the content of formaldehyde in this solution is preferably no more than 100 ppm by weight and more preferably no more than 50 ppm by weight.

The decomposition of urea may be performed by maintaining the urea melt in a reaction space, which is preferably maintained in a continuously stirred condition. The reaction space may consist of a series of reaction volumes.

Said biuret-forming conditions may include one or more of the following: a reaction temperature in the reaction space of 160° C. to 180° C., preferably 160° C. to 170° C. and more preferably 165° C.; a residence time in the reaction space that ranges from 30 min to 100 min, preferably 60 min; a pressure in the reaction space which is atmospheric pressure or below atmospheric pressure, preferably slightly below atmospheric pressure.

The decomposition of urea into biuret produces also a gaseous ammonia. An advantage of performing the decomposition at or about atmospheric pressure is that such gaseous ammonia can be easily condensed with the addition of a limited amount of water or with an aqueous process stream to produce an ammonia solution. Said ammonia solution may contain preferably 10% to 20% of ammonia. Said ammonia solution can be recycled to the urea plant to recover the ammonia contained therein. Another advantage is that no costly vacuum package is then required.

The decomposition of urea may be performed in a suitable biuret reactor, for example a continuously stirred reactor. Said reactor may include a reaction chamber surrounded by an interspace wherein hot steam is admitted to keep the reaction space inside the reaction chamber at the desired reaction temperature.

The high-biuret urea melt obtained after decomposition of urea, e.g. withdrawn from the biuret reactor, typically contains by weight 16% of biuret, less than 3% water and impurities (mainly cyanuric acid and triuret), the balance being urea.

The solution obtained after dilution of the high-biuret urea melt may contain by weight 40% to 60% of water, preferably 50%.

During crystallization, the solution is cooled down to a suitable temperature, for example 5° C., to obtain precipitation of biuret. The so obtained slurry is separated into a solid phase and a mother liquor. Said mother liquor typically contains by weight 2.0% to 3.0% of biuret, about 1.5% impurities (mainly cyanuric acid) and 40% to 50% urea.

The mother liquor from crystallization may be used as a cooling medium in a heat exchanger to cool the solution before crystallization. The mother liquor, possibly after this heat exchange step, may be recycled.

In an interesting embodiment the production of HBU is combined with the production of conventional low-biuret urea LBU. In that case, the urea solution from the recovery section may be split between a section for the production of HBU and a section for the production of LBU.

A more advanced level integration between the two processes is possible. The urea process typically includes a waste water treatment (WWT) section for the treatment of water removed from the solution, e.g. in an evaporation section. This WWT section usually encompasses a stripper/desorber to remove ammonia and $CO_2$ vapors and an hydrolyzer to convert urea to ammonia and $CO_2$.

As result the WWT section produces a carbonate solution, which is recycled to the urea recovery section, and an aqueous process condensate sent out of the battery limits. In an embodiment of the invention this process condensate can be used in the HBU section to dilute the high-biuret urea melt before crystallization and to condensate the gaseous ammonia released by the reactor. It has to be noted this process condensate can be used in the HBU section as it is, without the need to remove urea e.g. in a hydrolizer.

In a preferred embodiment of the invention the aqueous ammonia streams produced by the HBU section are treated in a dedicated ammonia stripper to remove ammonia and $CO_2$ from the process condensate.

Said dedicated ammonia stripper is operated preferably at about 2.6 barg (bar gauge) and provides the following streams: a carbonate solution which can be recycled to the recovery section of the urea plant; a process condensate practically free of ammonia and $CO_2$ that can be used for dilution of the high-biuret urea melt and/or for condensation of the ammonia released by the biuret reactor. The amount of said process condensate which exceeds the HBU process demand can be recycled to the WWT of urea plant.

More preferably said carbonate solution from the dedicated stripper may have a water content up to 65% wt. Said process condensate may contain less than 500 ppm of ammonia and $CO_2$ and up to 1.0% wt of urea.

A preferred embodiment includes that ammonia solution produced by condensation of the gaseous ammonia produced by the decomposition of urea is subject to ammonia stripping in a dedicated ammonia stripper, thus obtaining an aqueous process condensate and a carbonate recycle solution. Said recycle solution is sent to the urea recovery section and a first portion of said process condensate is used for the above mentioned condensation of gaseous ammonia. A second portion of said process condensate can be used to dilute the high-biuret urea melt. Also a waste water removed from the urea solution in the HBU section can be treated in said ammonia stripper.

The use of a dedicated ammonia stripper minimizes the impact of the HBU section on the WWT section of the urea plant.

In a preferred embodiment the heat to the dedicated stripper is indirectly provided by hot steam.

Dilution of the high-biuret urea melt with the process condensate from the WWT section or the dedicated ammonia stripper can be made preferably with a ratio 1:1 of said melt and process condensate.

A portion of said process condensate from the WWT section or the dedicated ammonia stripper can be used to help condensation of the gaseous ammonia removed from the biuret reactor. The ammonia solution obtained from such condensation of ammonia is recycled to the WWT section or the dedicated ammonia stripper, so that ammonia returns to the urea plant with the carbonate solution.

Another preferred feature is the removal of cyanuric acid from the mother liquor of crystallization. The mother liquor can be treated by adding an acid or carbon dioxide to reduce the pH of the liquor and facilitates the precipitation of cyanuric acid. Then the precipitated cyanuric acid can be removed for example by centrifugation. The amount of acid or carbon dioxide is preferably determined to lower the pH of the liquor to 7.2 or less.

Use of carbon dioxide for said treatment of the mother liquor offers a further possibility of integration because $CO_2$ is available as a source material for the production of urea. A stream of $CO_2$ can be taken from the $CO_2$ feed of the plant, for example from the delivery of the main $CO_2$ compressor. The gaseous ammonia is preferably absorbed in the mother liquor under pressure, preferably at a pressure of about 5 bar abs. The mother liquor may be pumped at such pressure if necessary.

The mother liquor, preferably after removal of cyanuric acid, can be recycled internally in the HBU section. Preferably said mother liquor is recycled to the water removal section (e.g. evaporator) of the HBU section. It must be noted that the HBU section and the LBU section have separate water removal sections. By recycling the mother liquor internally in the HBU section, a contamination of the LBU section with biuret it is avoided.

It can be understood from the above that a remarkable advantage of the invention is the strong integration between the production of conventional low-biuret urea and the production of high-biuret urea.

DESCRIPTION OF THE FIGURES

The invention and its advantages are now elucidated with the help of the figures wherein:

FIG. 1 illustrates a plant including a urea synthesis section 1, a recovery section 2, a high-biuret urea (HBU) section 3 and a low-biuret urea (LBU) section 4.

Figure 1:
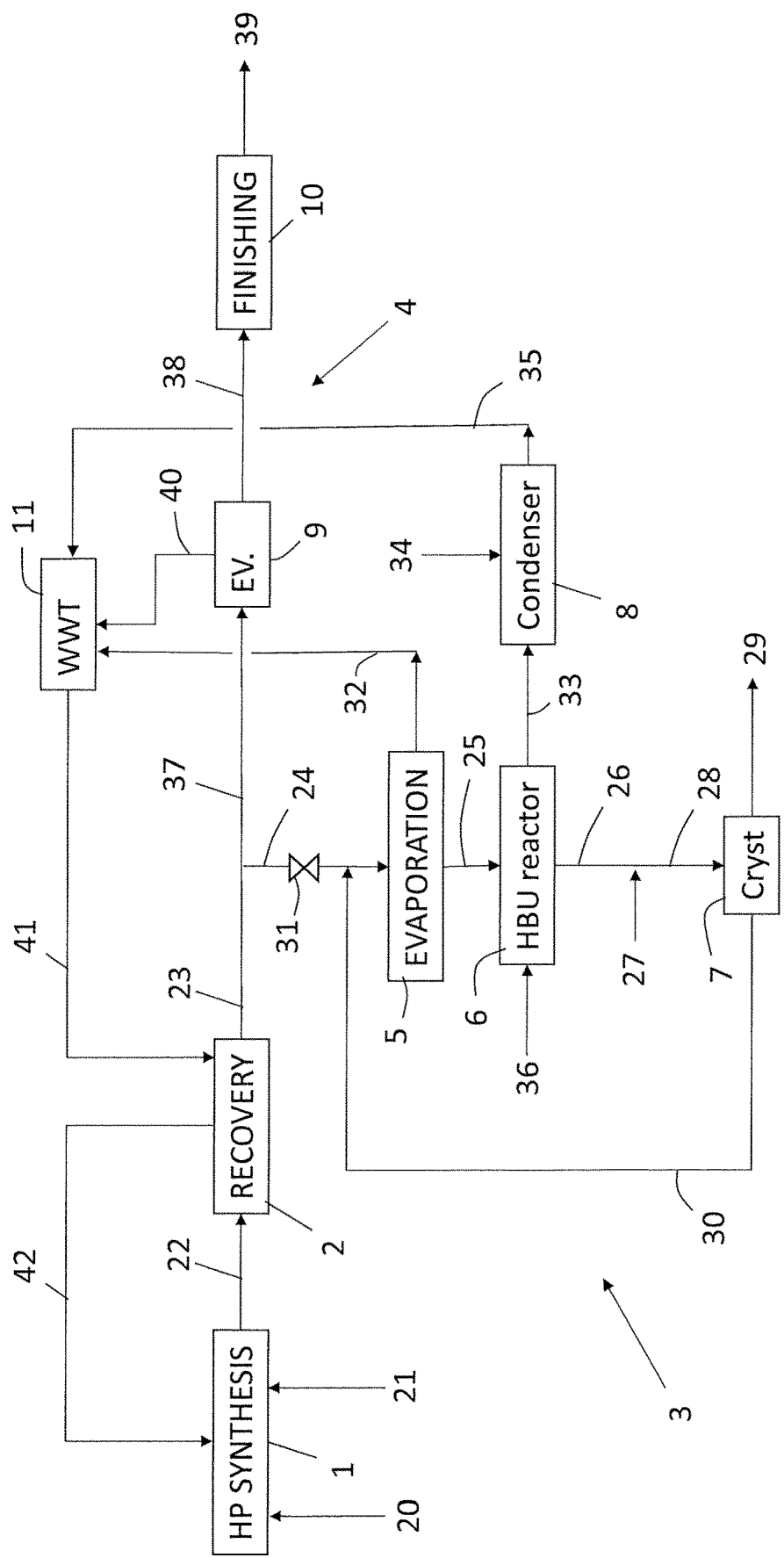
FIG. 1 illustrates a scheme of a first embodiment of combined production of low-biuret urea and high-biuret urea.

The HBU section 3 includes a first evaporator 5, biuret reactor 6, crystallization section 7 and ammonia condenser 8.

The LBU section 4 includes: a second evaporator 9, finishing section 10, waste water treatment section 11.

In FIG. 1, the following process streams are illustrated.
20 fresh carbon dioxide.
21 input of ammonia.
22 effluent from the synthesis section, which is typically a solution of urea, water and unconverted ammonium carbamate.
23 urea solution from the recovery section 2, which is predominantly urea and water with unavoidable impurities.
24 first portion of the urea solution 23, directed to the HBU section 3.
25 urea melt obtained in the evaporator 5 and fed to the HBU reactor 6. Said urea melt 25 typically contains more than 99% urea, e.g. 99.5% or more.
26 high-biuret urea melt obtained in the reactor 6. This melt may contain for example 16% biuret.
27 dilution water.
28 solution obtained from dilution of the high-biuret urea melt 26. This solution may contain for example 50% water, the balance being biuret and urea.
29 solid product obtained in the crystallization section 7.
30 mother liquor from crystallization, which is sent back to the evaporator 5.
31 valve controlling the flow rate of the portion 24 of urea solution.
32 water removed in the evaporator 5, which is sent to the WWT section 11.
33 gaseous ammonia produced by the thermal decomposition of urea and removed from the HBU reactor 6, which is sent to the ammonia condenser 8.
34 water for condensation of the ammonia 33.
35 ammonia solution recycled to the WWT section 11.
36 hot steam for heating the biuret reactor 6.
37 second portion of the urea solution 23, which is directed to the LBU section 4.
38 low-biuret urea melt from the evaporator 9.
39 low-biuret urea, e.g. granules or prills, produced in the finishing section 10.
40 water removed from the urea solution in the evaporator 9 and directed to the WWT section 11.
41 recycle solution from the WWT section 11 sent to the recovery section 2.
42 carbamate-containing solution obtained in the recovery section 2 and sent back to the synthesis section 1, e.g. to a high-pressure condenser.

Looking at FIG. 1 it can be appreciated that the urea solution 23 from the recovery section 2 is split into first portion 24 and second portion 37. The first portion 24 is used in the HBU section 3 for production of the high-biuret urea 29; the second portion 37 is used in the LBU section 4 for production of the low-biuret urea 39, for example fertilizer-grade urea.

The high-biuret urea melt 26, having for example a content of biuret of about 70 wt %, is diluted with water 27 until it contains around 50% water. The so obtained aqueous solution 28 is processed in the crystallization section 7 to obtain precipitation of biuret. In the crystallization section 7, the solution may be suitably cooled, e.g. to around 5° C., to obtain precipitation.

In the crystallization section 7, a slurry is obtained which is separated into a solid phase and a liquid phase represented by a mother liquor. Optionally the crystallization section 7 may include a drying section wherein the solid phase is processed to further remove water. Hence a solid product 29 and a mother liquor 30 are obtained. The solid product 29 may be a granular product or a powder.

It has to be noted that each of the HBU section 3 and LBU section 4 has a dedicated evaporator 5, 9. The provision of separate evaporators avoids contamination with biuret of the line dedicated to the production of LBU.

The water 32 removed from the evaporator 5 of the HBU section 3 and the ammonia condensate 35 are recycled to the WWT section 11, providing a first level of integration between the two sections 3 and 4.

The mother liquor 30 is recycled internally in the HBU section 3, by joining the feed of the evaporator 5, to avoid contamination of the LBU section, particularly of the evaporator 9.

Figure 2:
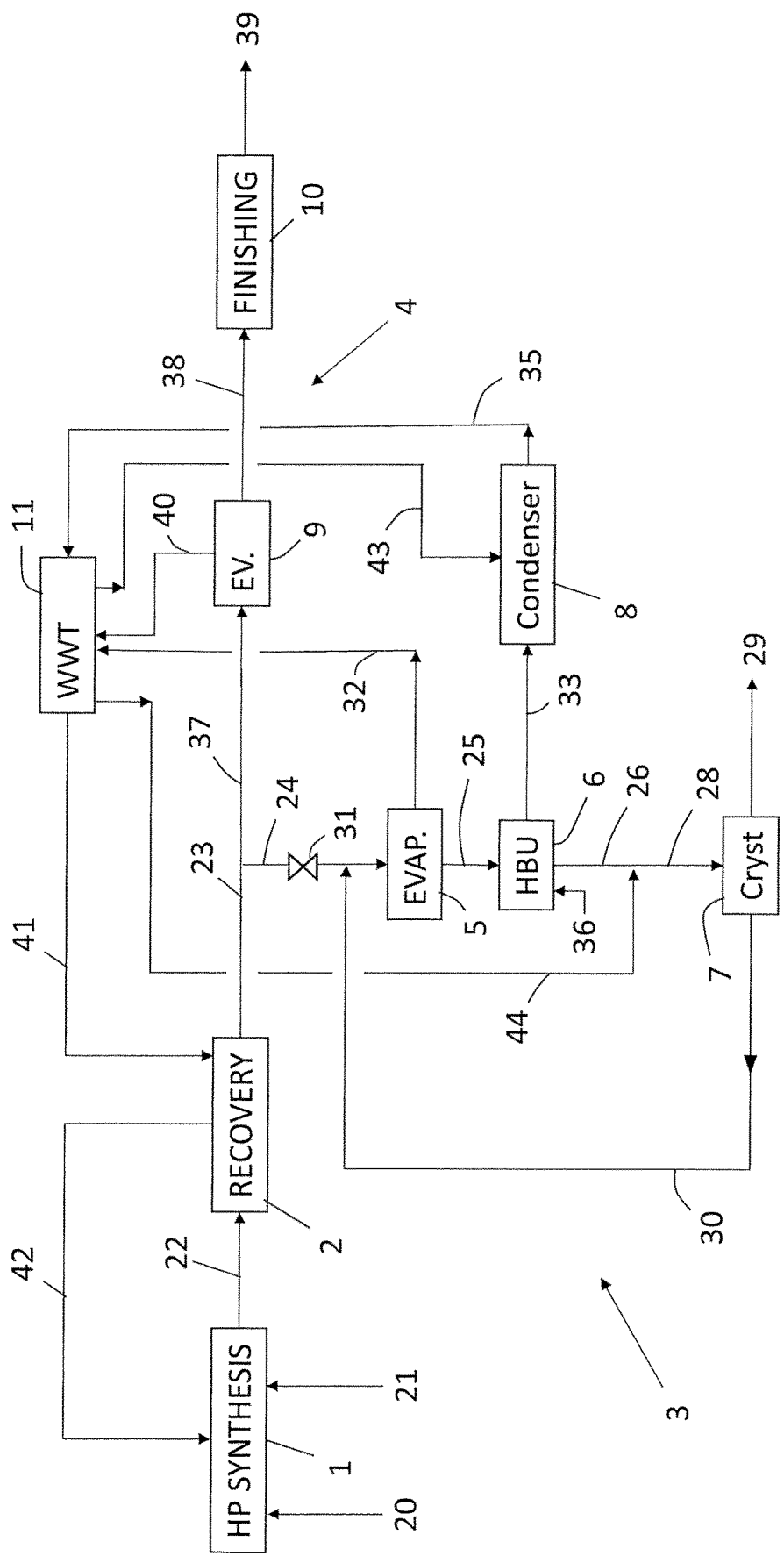
FIG. 2 is a variant of FIG. 1.

FIG. 2 is a variant providing a second level of integration wherein process condensate from the WWT section 11 is used instead of fresh water for diluting the high-biuret melt and to promote condensation of the ammonia removed from the reactor 6.

A first stream 43 of an aqueous process condensate from said WWT section 11 is used for condensation of ammonia instead of water 34; a second stream 44 of said process condensate is used to dilute the high-biuret melt 26 instead of water 27.

Figure 3:
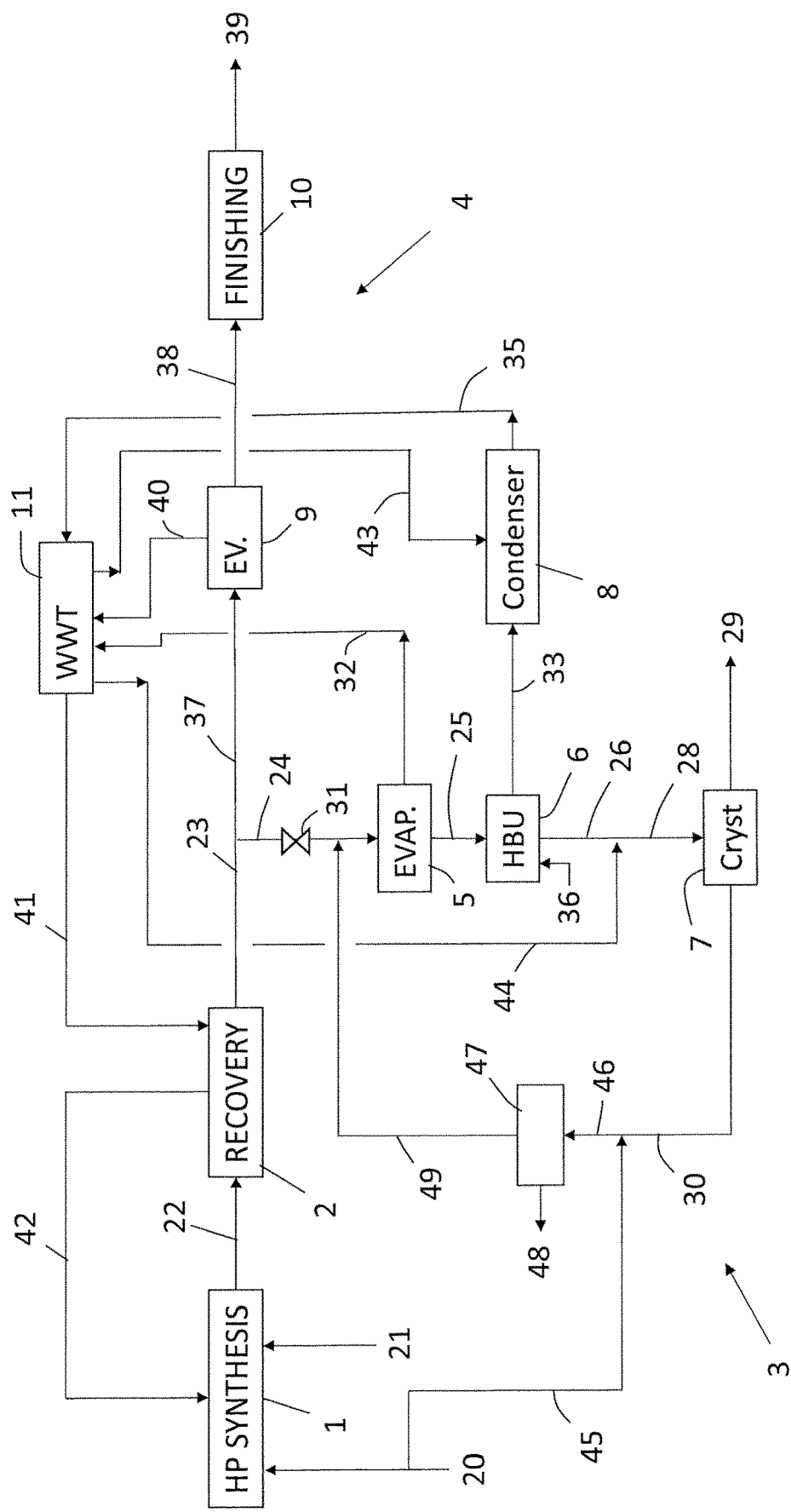
FIG. 3 is another variant of FIG. 1.

FIG. 3 illustrates a third level of integration wherein a portion of the $CO_2$ feed is used to remove cyanuric acid from the mother liquor 30 before it is recycled to the evaporator 5.

Particularly, a stream 45 of $CO_2$ taken from the $CO_2$ feed is absorbed in the liquor 30, obtaining a liquor 46 at a lower pH wherein the cyanuric acid precipitates. Then cyanuric acid is removed from said liquor 46 in a centrifuge 47 obtaining cyanuric acid solution 48 and a purified liquor 49 which is recycled to the evaporator 5.

Figure 4:
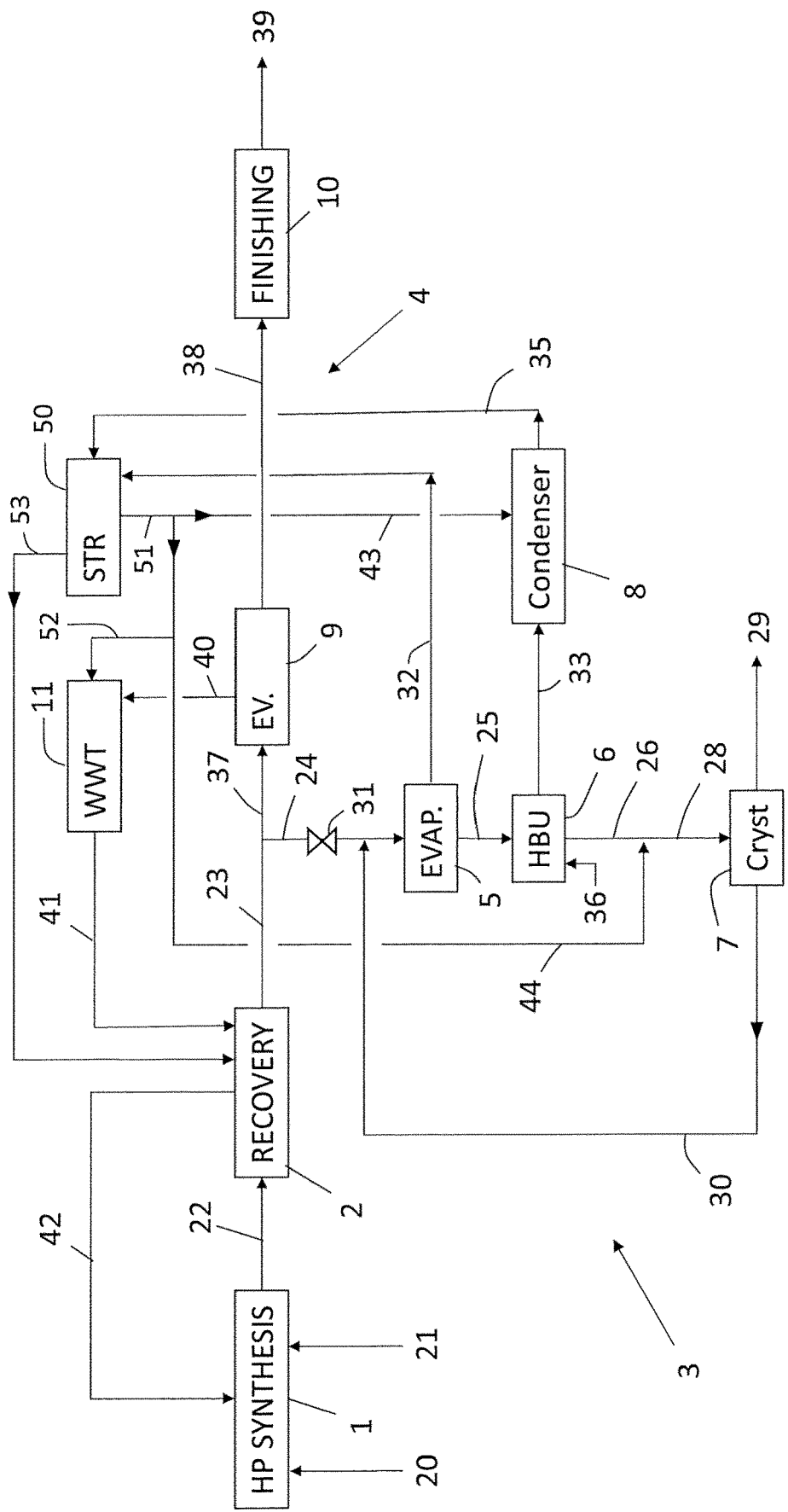
FIG. 4 is a variant of FIG. 1 with dedicated ammonia stripper

FIG. 4 illustrates a further embodiment including a dedicated stripper 50 for the HBU unit 3. Said stripper 50 receives the water stream 32 and ammonia solution 35 and produces a process condensate 51. Said condensate 51 forms a condensation stream 543 and the dilution stream 544 whose function is similar to streams 43, 44 as above disclosed. Another part of said condensate 51 is sent to the WWT section 11 as stream 52.

The stripper 50 additionally produces a second carbonate recycle solution 53 which is sent to the recovery section 2 in addition to the recycle solution 41.

The stripper 50 illustrated in FIG. 4 may be implemented in all the embodiments of the invention, for example the embodiment of FIG. 3. The stripper 50 may be also integrated in the WWT section 11.

What is claimed is:

1. A process for the production of biuret from urea comprising:
    a) ammonia and carbon dioxide are reacted in a synthesis section at a synthesis pressure to form urea and obtaining a reaction effluent containing urea, water and unconverted reagents;
    b) said reaction effluent is processed in a recovery section to recover unconverted reagents contained therein;
    c) a urea aqueous solution, withdrawn from the recovery section, is processed to remove water and obtain a concentrated urea melt; said urea aqueous solution containing no more than 100 ppm by weight of formaldehyde;
    d) said urea melt is processed under biuret-forming conditions to decompose urea into biuret and ammonia and obtain a biuret urea melt;
    e) said biuret urea melt is diluted with water or with an aqueous stream obtaining a solution;
    f) the solution obtained at step e) is subject to a process of crystallization including precipitation of a solid phase containing biuret and obtaining a slurry including precipitated solid phase and a mother liquor;
    g) the slurry obtained at step f) is processed to obtain a biuret-containing solid product and a mother liquor.

2. The process according with claim 1, wherein the step g) includes separation of a solid phase from the slurry and further processing of said solid phase to remove residual water.

3. The process according to claim 1, wherein the solid product obtained after step g) contains at least 55% by weight of biuret.

4. The process according to claim 1, wherein the sum of biuret and urea in the solid product obtained after step g) is at least 80% by weight.

5. The process according to claim 1, wherein step d) is performed by maintaining the urea melt in a reaction space.

6. The process according to claim 5, wherein the biuret-forming conditions of step d) include one or more of:
    a reaction temperature in the reaction space of 160° C. to 180° C.;
    a residence time in the reaction space that ranges from 30 min to 100 min;
    a pressure in the reaction space which is atmospheric pressure or slightly below atmospheric pressure.

7. The process according to claim 1, wherein the urea aqueous solution of step c) is free of formaldehyde.

8. The process according to claim 1, wherein:
    the urea aqueous solution of step c) is a first portion of a solution obtained from the recovery section;
    a second portion of urea aqueous solution from the recovery section is processed to remove water, separately from the first portion, obtaining a urea melt;
    said urea melt obtained from the second portion of the solution is processed for the production of low-biuret urea.

9. The process according to claim 1, wherein the solution obtained after dilution of step e) contains by weight 40% to 60% of water.

10. The process according to claim 1, wherein gaseous ammonia obtained at step d) is condensed obtaining an ammonia solution and ammonia contained in said solution is recycled to the urea process.

11. The process according to claim 10, wherein said gaseous ammonia is condensed with process condensate from a waste water treatment section and the ammonia solution is recycled to said waste water treatment section.

12. The process according to claim 10, wherein the ammonia solution is subject to ammonia stripping in a dedicated ammonia stripper, thus obtaining an aqueous process condensate and a carbonate recycle solution;
    said recycle solution is sent to the urea recovery section;
    a first portion of said process condensate is used for condensation of said gaseous ammonia.

13. The process according to claim 12, wherein: a waste water obtained at step c) is treated in said ammonia stripper and a second portion of said process condensate is used in step e) to dilute the biuret urea melt.

14. The process according to claim 1, wherein the mother liquor obtained at step f) is treated by adding an acid or carbon dioxide to reduce the pH of the liquor, and cause the precipitation of cyanuric acid contained in the liquor, and the precipitated cyanuric acid is removed.

15. The process according to claim 14, wherein the mother liquor is treated by absorption of gaseous carbon dioxide and the absorption is performed under pressure.

16. The process according to claim 1, wherein the mother liquor of step f) is mixed with the urea solution of step c) before the water removal step.

17. The process according to claim 1, wherein said urea aqueous solution contains no more than 50 ppm by weight of formaldehyde.

18. The process according to claim 1, wherein the solid product obtained after step g) contains at least 70% by weight of biuret.

19. The process according to claim 1, wherein step d) is performed by maintaining the urea melt in a reaction space in a continuously stirred condition.

20. The process according to claim 5, wherein the biuret-forming conditions of step d) include one or more of:
a reaction temperature in the reaction space of 160° C. to 170° C.;
a residence time in the reaction space that ranges from 30 min to 100 min;
a pressure in the reaction space which is atmospheric pressure or slightly below atmospheric pressure.

21. The process according to claim 5, wherein the biuret-forming conditions of step d) include one or more of:
a reaction temperature in the reaction space of 165° C.;
a residence time in the reaction space that ranges from 30 min to 100 min;
a pressure in the reaction space which is atmospheric pressure or slightly below atmospheric pressure.

22. The process according to claim 1, wherein the solution obtained after dilution of step e) contains by weight 50% of water.

23. The process according to claim 1, wherein the mother liquor obtained at step f) is treated by adding an acid or carbon dioxide to reduce the pH of the liquor to 7.2 or less, and cause the precipitation of cyanuric acid contained in the liquor, and the precipitated cyanuric acid is removed.

24. The process according to claim 14, wherein the mother liquor is treated by absorption of gaseous carbon dioxide and the absorption is performed at a pressure of about 5 bar abs.

25. The process according to claim 1, wherein the mother liquor of step f), after removal of cyanuric acid, is mixed with the urea solution of step c) before the water removal step.

* * * * *